US009925070B2

(12) United States Patent
Nakaya et al.

(10) Patent No.: US 9,925,070 B2
(45) Date of Patent: Mar. 27, 2018

(54) HERMETICALLY SEALED ARTIFICIAL LEG

(75) Inventors: Yoshiaki Nakaya, Kobe (JP); Taishiro Misao, Kobe (JP); Hiroaki Hashimoto, Kobe (JP); Nobuyuki Nakamura, Kobe (JP); Yoshihiro Tada, Kobe (JP)

(73) Assignee: NABTESCO CORPORATION, Tokyo (JP)

(*) Notice: Subject to any disclaimer, the term of this patent is extended or adjusted under 35 U.S.C. 154(b) by 0 days.

(21) Appl. No.: 14/424,239

(22) PCT Filed: Aug. 30, 2012

(86) PCT No.: PCT/JP2012/072029
§ 371 (c)(1),
(2), (4) Date: May 18, 2015

(87) PCT Pub. No.: WO2014/033876
PCT Pub. Date: Mar. 6, 2014

(65) Prior Publication Data
US 2015/0250622 A1 Sep. 10, 2015

(51) Int. Cl.
*A61F 2/64* (2006.01)
*A61F 2/50* (2006.01)
(Continued)

(52) U.S. Cl.
CPC ............. *A61F 2/64* (2013.01); *A61F 2/66* (2013.01); *A61F 2/70* (2013.01); *F16J 9/00* (2013.01);
(Continued)

(58) Field of Classification Search
CPC .. A61F 2/64; A61F 2/642; A61F 2/644; A61F 2/646; A61F 2/66; A61F 2/6607;
(Continued)

(56) References Cited

U.S. PATENT DOCUMENTS 2,397,597 A * 4/1946 Dunkle .................. F16L 23/20
277/649
2,774,621 A * 12/1956 Kilbourne, Jr. ......... F16L 23/22
277/649
(Continued)

FOREIGN PATENT DOCUMENTS

GB 2108217 A * 5/1983 ............. F16J 15/123
JP 55-130657 A 10/1980
(Continued)

OTHER PUBLICATIONS

International Preliminary Report on Patentability and the Written Opinion of the International Searching Authority as issued in International Application No. PCT/JP2012/072029, dated Mar. 3, 2015 (Forms PCT/IB373 & PCT/ISA/237).
(Continued)

Primary Examiner — Thomas J Sweet
Assistant Examiner — Christie Bahena
(74) Attorney, Agent, or Firm — Pillsbury Winthrop Shaw Pittman, LLP

(57) ABSTRACT

This invention relates to a technique for hermetically sealing an artificial leg including a cylinder device. A rod member of the cylinder device extends from the inside to the outside of a shell structure of the cylinder device. The rod member is hermetically sealed at the periphery thereof by a bellows packing member. The bellows packing member comprises an inner bead, an outer bead which concentrically surrounds the outside of the inner bead, and a bellows packing body part which connects the inner and outer beads. The bellows packing body part includes corrugations, and each corrugation is less curved than an imaginary circle which is concentric with the inner bead and the outer bead. Both ends of each of the plurality of corrugations extend to the outer bead (Continued)

or are located at positions closer to the outer bead than the inner bead.

15 Claims, 8 Drawing Sheets

(51) Int. Cl.
    *A61J 9/00*           (2006.01)
    *F16J 9/00*          (2006.01)
    *A61F 2/66*          (2006.01)
    *A61F 2/70*          (2006.01)
    *A61F 2/60*          (2006.01)

(52) U.S. Cl.
    CPC ................ *A61F 2002/5006* (2013.01); *A61F 2002/5039* (2013.01); *A61F 2002/607* (2013.01)

(58) Field of Classification Search
    CPC ................ A61F 2/78; A61F 2002/5006; A61F 2002/74; A61F 2002/745; F16L 23/22; F16L 23/24; Y10S 285/91; F16J 15/16; F16J 9/064; F16J 9/067; F16J 9/068; F16J 9/069; F16J 3/00; F16J 3/02; F16J 3/04; F16J 3/06; F16J 3/066; F16J 3/08; F16J 3/10; F16J 3/20; F16J 3/28; F16J 15/50; F16J 15/52; F16J 15/56; A16J 9/063; A16J 9/069; A16J 9/08; A16J 9/10; A16J 9/12; A16J 9/14; A16J 9/145; A16J 9/16; A16J 9/18; A16J 9/20; A16J 9/203; A16J 9/206; A16J 9/22; A16J 9/24; A16J 9/26; A16J 9/28
    See application file for complete search history.

(56) References Cited

U.S. PATENT DOCUMENTS

| | | | | |
|---|---|---|---|---|
| 2,983,533 | A | * | 5/1961 | Tisch ....................... F16J 15/32 277/649 |
| 3,542,382 | A | * | 11/1970 | Hagmann .............. F16J 15/123 277/649 |
| 4,310,932 | A | | 1/1982 | Näder et al. |
| 5,232,229 | A | * | 8/1993 | Udagawa ............. F16J 15/0825 277/595 |
| 5,248,154 | A | * | 9/1993 | Westhoff ................... F16L 5/10 277/606 |
| 5,507,420 | A | * | 4/1996 | O'Neill ................. B65D 83/60 141/20 |
| 5,893,891 | A | * | 4/1999 | Zahedi ...................... A61F 2/68 623/24 |
| 5,948,021 | A | | 9/1999 | Radcliffe |
| 6,092,811 | A | * | 7/2000 | Bojarczuk .............. F16J 15/122 277/627 |
| 6,558,430 | B1 | * | 5/2003 | Nakaya ..................... A61F 2/64 188/313 |
| 6,845,983 | B1 | * | 1/2005 | Suggs .................... F16J 15/064 277/314 |
| 2005/0111689 | A1 | * | 5/2005 | True ........................ H04R 7/20 381/423 |
| 2007/0156252 | A1 | | 7/2007 | Jonsson et al. |
| 2010/0191347 | A1 | * | 7/2010 | Pusch ........................ A61F 2/60 623/27 |
| 2012/0112420 | A1 | * | 5/2012 | Stetter ................. F16J 15/0825 277/593 |
| 2012/0283845 | A1 | * | 11/2012 | Herr ......................... A61F 2/66 623/24 |

FOREIGN PATENT DOCUMENTS

| | | |
|---|---|---|
| JP | 07-308332 A | 11/1995 |
| JP | 2001-137268 A | 5/2001 |
| JP | 2002-058689 A | 2/2002 |
| JP | 2010-075727 A | 4/2010 |

OTHER PUBLICATIONS

International Search Report as issued in International Patent Application No. PCT/JP2012/072029, dated Nov. 6, 2012.

Extended European Search Report as issued in European Patent Application No. 12888769.7, dated Apr. 20, 2016.

* cited by examiner

HERMETICALLY SEALED ARTIFICIAL LEG

CROSS-REFERENCE TO RELATED APPLICATION

This application is the U.S. National Stage of PCT/JP2012/072029, filed Aug. 30, 2012. The content of this application is incorporated herein by reference in its entirety.

TECHNICAL FIELD

This invention relates to a technique capable of effectively exhibiting the function of waterproof and dustproof of an artificial leg which includes a cylinder device for assisting or limiting the movement of the knee coupling, and more particularly to a technique for hermetically sealing the periphery of a rod member extending to the outside of a shell structure while utilizing the shell structure which surrounds the outside of the cylinder device.

BACKGROUND ART

In general, an artificial leg including a knee coupling or a knee joint comprises an upper member for supporting a socket at its upper end, a lower member for supporting a foot part at its end, and a knee coupling for bendably coupling the upper and lower members, and a cylinder device for assisting or limiting the movement of the knee coupling.

As a cylinder device for assisting or limiting the movement of a knee coupling, a linear actuator is known in addition to a hydraulic cylinder, a spring cylinder and a pneumatic cylinder. The first-mentioned linear actuator generates a self-driving force by a motor. On the other hand, anyone of the various cylinders which belong to the second-mentioned group generates a resisting force against the force or movement produced by the wearer of the artificial leg. However, the form of the cylinder device is the same regardless whether the cylinder device is the first-mentioned one or anyone of the second-mentioned group. That is, the cylinder device comprises a cylinder body, which is a casing having a comparatively large diameter, containing a piston and a spring therein (in the case of the linear actuator, a body casing containing a motor therein), and a rod member, which is an elongated member having a smaller diameter than the cylinder body, extending from the cylinder body.

The conventional artificial leg having such a cylinder device as just mentioned is a sort of open-type which is provided with an inlet port and is obliged to allow foreign matters (water, sweat, dust, etc.) to enter therein from outside. The reasons why the open-type is obliged to be employed or why entrance of foreign matters is unavoidable are considered to reside in that the cylinder device, particularly the rod member thereof performs a unique movement in accordance with the movement of the artificial leg. When the upper and lower members are move or bend with respect to each other, the rod member is expanded and contracted in the axial direction of the cylinder body and at the same time, swung in the direction crossing the axis. For example, the expanding and contracting amount of the rod member is about 35 mm or larger and its swinging angle is about 10 degrees or larger.

PRIOR ART PATENT DOCUMENTS

For example, Patent Document 1 shows an artificial leg having a pneumatic cylinder; Patent Document 2, an artificial leg having a hydraulic cylinder; and Patent Document 3, an artificial leg having a spring cylinder, respectively. Moreover, Patent Document 4 shows a linear actuator.

Patent Document 1: Official Gazette of Japanese Patent Application Laid-Open No. 2001-137268
Patent Document 2: Official Gazette of Japanese Patent Application Laid-Open No. 2002-58689
Patent Document 3: Official Gazette of Japanese Patent Application Laid-Open No. Sho-55 (1980)-130657
Patent Document 4: Official Gazette of Japanese Patent Application Laid-Open No. 2010-75727

SUMMARY OF INVENTION

Problems to be Solved by Invention

An artificial leg having a cylinder device inherently includes factors which make it difficult to be formed of a hermetically sealed type. Nevertheless, it is demanded for such an artificial leg to be formed of a hermetically sealed type, partly because the cylinder device itself inherently hates such foreign matters as water (moisture), dust, etc. In addition, if foreign solid matters such as metal screws, pins, etc. should enter into the artificial leg and held between the cylinder device and the frame of the artificial leg, the cylinder portion of the cylinder device or its rod portion would be broken. Moreover, in order to spend a normal daily life comfortably, it is required that the electronic parts for controlling the artificial leg are provided with the waterproof function as well as the dust-proof function.

As one method for providing such water-proof function and dust-proof function, it can be considered that electronic parts for electronically controlling a control circuit such as a cylinder device, a battery, a storage part thereof and a sensor part are individually hermetically sealed. However, the parts which require water-proofing are too many and too complex. Thus, it is difficult to totally effectively hermetically seal them as a whole.

It is, therefore, an object of the present invention to provide a technique capable of hermetically sealing an artificial leg as a whole rather than individually sealing each location of the respective parts.

Another object of the present invention is to provide a technique capable of effectively hermetically sealing the periphery of a movable rod member by bellows packing member, while effectively utilizing a shell structure surrounding the outside of a cylinder device. Other objects of the present invention will become manifest from the description to follow.

Means to Solve Problems

According to the present invention, the water-proof function and dust-proof function are provided to the shell structure surrounding the outside of the cylinder device. For this purpose, the shell structure itself is configured to have a structure suitable to seal. For example, the shell structure comprises a frame serving as a main body and a frame cover for covering an opening part of the frame. Preferably, a frame packing is disposed between the frame and the frame cover in order to provide a favorable hermetical sealing.

When the movement of the rod member is taken into account, it can be considered that the entire circumference capable of covering the movement of the rod member is covered with the shell structure. In doing so, however, the shell structure becomes bulky and impractical from the viewpoint of design of the artificial leg or the like. According to the present invention, a part of the rod member is located on the outside of the shell structure. Therefore, a part of the rod member extends from the cylinder body within the shell structure to the outside of the shell structure.

According to the present invention, the rod member, which extends from the inside to the outside of the shell structure, is hermetically sealed at a periphery thereof by a bellows packing member. The bellows packing member includes and/or satisfies the following constitution and/or conditions.

(i) an inner bead defining a hole for receiving the rod member therein and serving as a sealing portion for an inner periphery of the bellows packing member;

(ii) an outer bead serving as an attachment part to the shell structure side and also serving as a sealing portion for the shell structure side;

(iii) a bellows packing body part which is a body portion located between the inner and outer beads and which has a plurality of irregular corrugations aligned with each other and which is capable of varying a distance between the inner and outer beads; and (iv) each of the plurality of corrugations is less curved than an imaginary circle which is a concentric circle with the inner bead and the outer bead and is located between the inner and outer beads, each of the plurality of corrugations is positioned between the inner bead and the outer bead, and both ends of each of the plurality of corrugations extend to the outer bead or are located at positions closer to the outer bead than the inner bead.

The bellows packing member, in corporation with the shell structure, defines a hermetically sealed space within the shell structure. Owing to the foregoing arrangement, the entire cylinder device only excluding a part of the rod member can be received in the hermetically sealed space. Moreover, the parts for electronic control of the artificial leg can also be received in the hermetically sealed space. The hermetically sealed space is a space into which no foreign matters such as moisture, dust, etc. can enter from outside. Therefore, the cylindrical device and the parts in the hermetically sealed space can keep a high reliability, without trouble which will otherwise be caused by foreign matters.

The bellows packing member employed in the present invention normally exhibits the hermetically sealing function without jeopardizing the movement of the artificial leg. The details and features of the bellows packing member will now be described with reference to its relation to the movement of the artificial leg.

When the upper and lower members move or bend with respect to each other, the rod member of the cylinder device performs two movements at the same time. The first movement is that the rod member is expanded and contracted in an axial direction of the cylinder body, and the second movement is that the rod member is swung in a direction crossing the axis. In order to respond to the expanding and contracting movement (i.e., the first movement), the bellows packing member includes an inner bead that has a hole for allowing the rod member to be received therein. In order to achieve hermetical sealing, it is required that the inner bead is provided at an inner periphery thereof with a sealing part. It is demanded to obtain an effective and reliable sealing function under the mutually different first and second movements. In this respect, it is preferable that a rod guide is provided on the side of the cylinder body, so that the rod guide guides the rod member and supports the inner bead. In general, the rod guide has a cylindrical shape and is provided at an inner periphery thereof with a guide surface for guiding an outer periphery of the rod member, and at an outer periphery thereof with a ring groove into which the inner bead is received.

The second movement is a swinging movement in a direction crossing the direction of the first movement. Since the second movement is taken place in accompany with the bending movement of the artificial leg, the swinging movement (swinging movement of the rod member) is a movement in a predetermined direction along the walking direction and its swinging distance is also limited (for example, 10 through 20 degrees in a swinging angle-wise distance). Such swinging movement is smaller in the case where the connection is made by a multi-axis connection, i.e., with the use of an articulated link than in the case where the connection is made by a single axis connection. The smaller swinging movement means that the amount of deformation needed by the bellows packing member side becomes smaller. The bellows packing member having a small amount of deformation is advantageous not only in durability but also sealability. For this reason, the present invention is favorably applicable to an artificial leg in which the connection is made by a multi-axis connection, but not limited thereto.

The bellows packing member includes an outer bead at the outside of an inner bead. A bellows packing body part is formed between the outer and inner beads. The bellows packing body part has a plurality of irregular or wavy corrugations aligned with each other and those corrugations are expanded and contracted like the bellows, thus enabling to vary the distance between the outer and inner beads. The variable distance is set to long enough to cover the second movement.

The outer bead of the bellows packing member is fitted to the shell structure side, in general, into a ring groove formed in a frame such that it is supported in a sealed state. Since both the outer and inner beads are supported in a sealed state, the periphery of the rod member is effectively hermetically sealed.

Here, the bellows packing body part is normally deformed in accordance with the movement of the artificial leg. This deformation is made in the predetermined radial directions of the outer bead. As a result of our study through experiments, it became apparent that when a plurality of corrugations of the bellows packing body part are concentrically arranged, the corrugations are vertically warped and tend to generate a deformation sound. Such deformation sound tends to be taken as noise by the artistic leg wearer which might give a sense of anxiety or discomfort to the wearer.

In the present invention, by arranging each corrugation in such a manner as not to form a closed loop state, when each corrugation is deformed in accordance with the swinging movement of the rod member, the deformed part hardly exerts an adverse effect to the rest part continuous thereto. More specifically, each of the corrugations is less curved than an imaginary circle (i.e., concentric circle) between the inner and outer beads and is configured in such a manner that both ends of each corrugation reach or extend to the outer bead or are located at positions closer to the outer bead than the inner bead. Owing to the foregoing arrangement, noise caused by deformation can be prevented from occurring, or noise can be reduced.

Regarding the arrangement of the cylinder device, the cylinder body having a larger diameter is disposed under the rod member and the rod member having a smaller diameter is disposed thereabove. There are two types: in one type, the rod member is disposed above the cylinder body and in the other type, the rod member is disposed under the cylinder body in which the vertical relation between the cylinder body and the rod member is reverse. The present invention is more favorably applicable to an artificial leg of the first type in which the rod member is disposed above the cylinder body rather than that of the second type in which the rod member is disposed under the cylinder body. The first type in which the rod member is disposed above the cylinder body is preferable from also the viewpoint of design performance and/or load applicable to the wiring, etc. in connection with electronic control.

The bellows packing member including the inner and outer beads and bellows packing body part may be composed of various rubber materials (for example, chloroprene rubber, silicone rubber, etc.) or a fiber-reinforced rubber material, etc. In that case, in order to enhance the durability of the material, it is preferable to design such that a deformation amount corresponding to the swinging movement of the rod member by the spread (or folding) of the corrugations can be obtained instead of expecting the elongation of the materials.

From the view point of reducing the space occupied by the bellows packing member for hermetically sealing the periphery of the rod member, it is preferable to provide a flat type in which the inner and outer beads are in the same height in a sectional view taken in the longitudinal direction of the rod member. In the alternative, a three-dimensional type may be employed in which the heights of the inner and outer beads are different from each other (for example, the inner bead is located in a position closer to the rod end of the rod member than the outer bead).

BEST MODE FOR CARRYING OUT THE INVENTION

Figure 1:
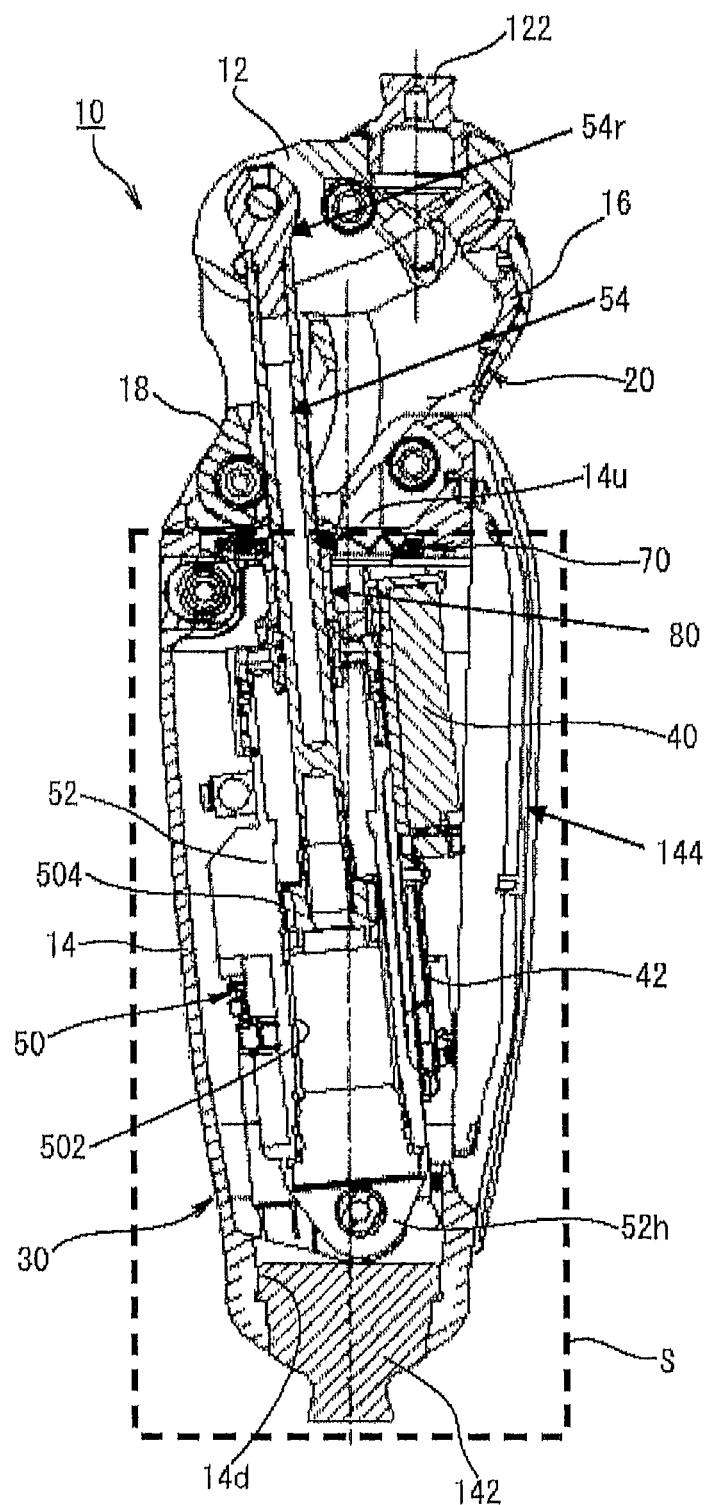
FIG. 1 is a sectional structural view of an artificial leg according to one embodiment of the present invention, in which a knee coupling is in a fully extended state.
Figure 2:
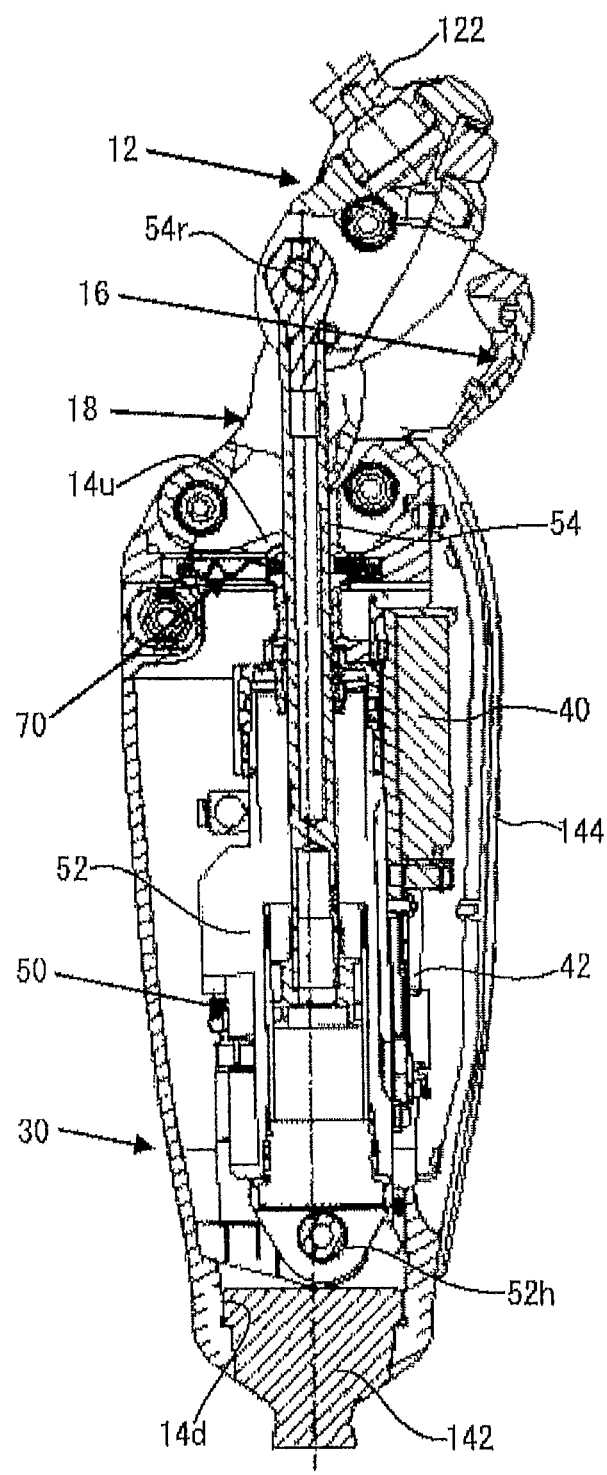
FIG. 2 is a sectional structural view of the artificial leg of FIG. 1, in which the knee coupling is in a bent state.
Figure 3:
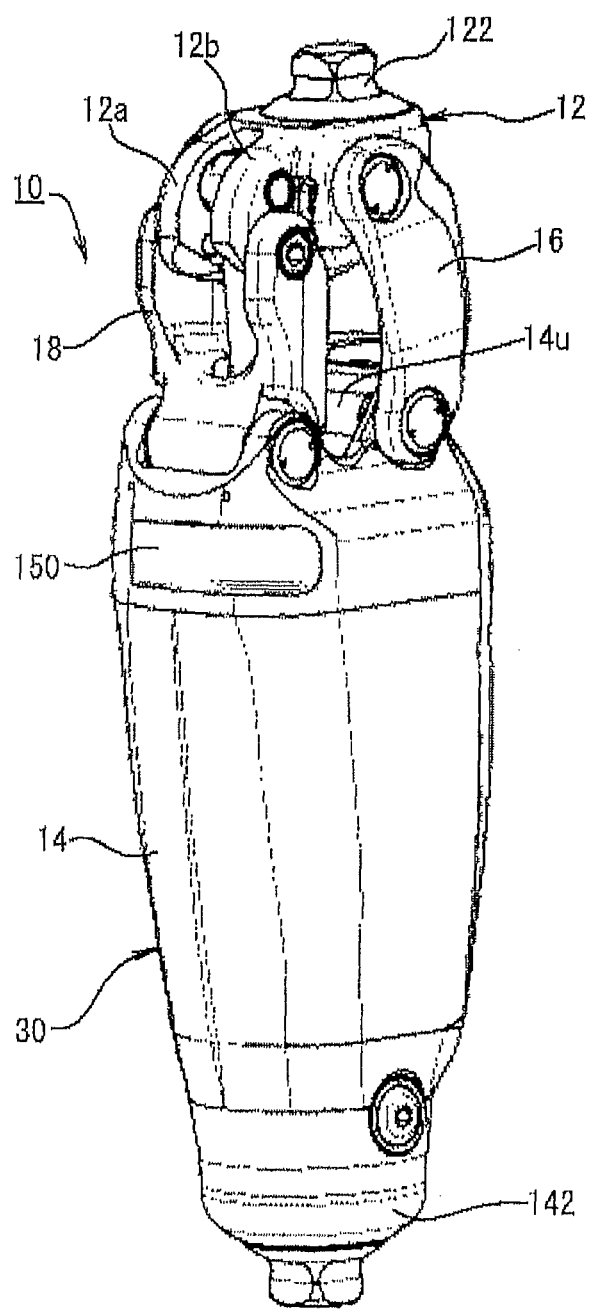
FIG. 3 is a perspective view showing an outer appearance of the artificial leg of FIG. 1.

FIGS. 1 through 3 show a multi-axis artificial leg according to one embodiment of the present invention, and especially, it shows a knee coupling portion thereof mostly. An artificial leg 10, which is a thigh artificial leg, comprises an upper member 12 located at an upper side of the knee, and a lower member 14 located at a lower side of the knee and bendably or swingably connected to the upper member 12 so as to enable the knee to bend. The upper member 12 integrally supports at an upper central part thereof an alignment member 122. An alignment member 122 is adapted to attach a socket, not shown, thereto. The alignment member 122 supports the load of a wearer of the artificial leg 10 through a thigh part that is received in the socket. On the other hand, the lower member 14 is also provided at a lower central part thereof with another alignment member 142. This alignment member 142 is adapted to attach a leg member that supports a foot part, thereto.

The upper and lower members 12, 14 are coupled to each other through a knee coupling 20. The knee coupling 20 is composed of a four-node or four bar link mechanism. The four-node or four bar link mechanism is a constrained chain that is obtained by rotatably connecting four links. Each of the above-mentioned upper and lower members 12, 14 functions as one of the four links of the constrained chain. One of the remaining two links is a front link 16 and the other is a rear link 18. Each of those two links 16 and 18 has a laterally symmetrical configuration, and an upper connection part and a lower connection part thereof form a pair laterally. Thus, the front and rear links 16 and 18, which are vertically spaced apart, surround the outside of the knee coupling 20 in cooperation with each other.

Here, the upper member 12 has a plate-like configuration that includes two plate parts 12a, 12b, while the lower member 14 has a frame-like configuration that defines an internal space. The frame 14, which is a lower member, has an upper opening 14u at an upper side facing the upper member 12 and a lower opening 14d at a lower side opposite thereto. The frame 14 has a front opening at a front surface portion facing the internal parts (for example, a battery and a control board).

In the artificial leg 10, a shell structure 30, which defines an internal space, is composed of the frame 14 (i.e., the lower member). Received in the internal space are a battery 40 and a control member or substrate 42 for electronic control, and a hydraulic cylinder 50 for assisting or limiting the movement of the knee coupling 20. Thus, the lower opening 14d of the frame 14 is hermetical sealed by the alignment block 142, and the front opening is hermetically sealed by a frame cover 144 in cooperation with the frame packing. By virtue of the foregoing arrangement, a waterproof property and a dust-proof property can be provided to the peripheral side surface and the lower part of the shell structure 30 surrounding the hydraulic cylinder 50 (i.e., the cylinder device).

In order to form the artificial leg 10 into a hermetically sealed type, it is required to completely block the internal space of the shell structure 30, which is chiefly composed of the frame 14, from outside. For this purpose, the portion of an upper opening 14u of the frame 14 is required to be effectively hermetically sealed.

In this invention, the portion of the upper opening 14u, i.e., the upper opening of the shell structure 30 is hermetically sealed by the specific bellows packing member 70. As a result, the artificial leg 10 is formed into the hermetically sealed type in which the portion S indicated by broken lines in FIG. 1 is waterproofed and dustproofed by the shell structure 30 and the bellows packing member 70.

The hydraulic cylinder 50, which is the cylinder device, comprises a cylinder body 52 adapted to define a cylinder hole 502 and containing a piston 504 in the cylinder hole 502, and a rod member 54 supporting the piston 504 at one end thereof and extending from the cylinder body 52 and then passing through the upper opening 14u so as to be supported by the upper member 12. In the hydraulic cylinder 50, a head end 52h of the cylinder body 52 is rotatably supported by a lower part of the frame 14 and a rod end 54*r* of the rod member 54 is rotatably supported by the upper member 12.

It is well known that such hydraulic cylinder 50 limits the movement of the knee coupling 20 in accordance with the flow resistance of the hydraulic oil passing through a restriction. As can be seen from the comparison between FIG. 1 showing a fully extended state and FIG. 2 showing a slightly extended state, when the knee coupling 20 is moved, the rod member 54 is expanded and contracted with respect to the cylinder body 52 and swung about the supporting point of the portion of the head end 52*h* together with the cylinder body 52.

Figure 4:
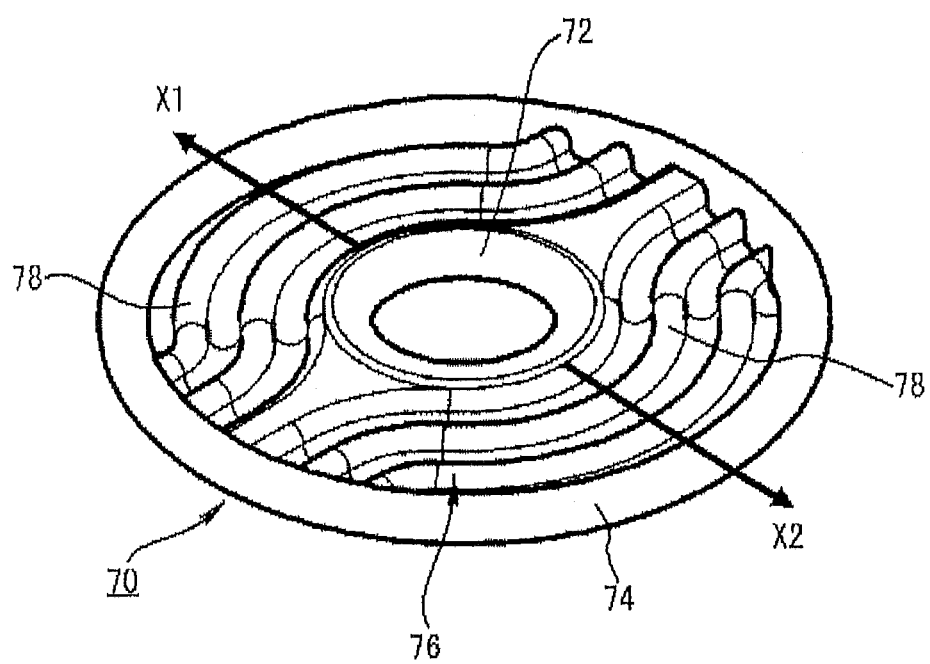
FIG. 4 is a perspective view showing a first example of a bellows packing member used in the present invention.
Figure 5:
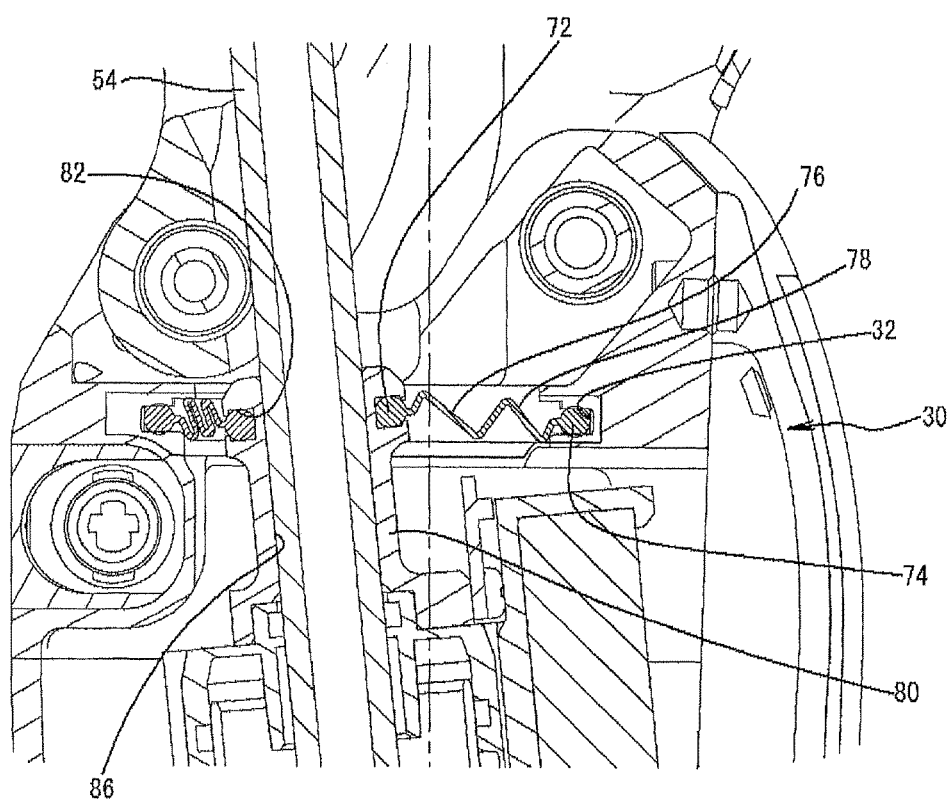
FIG. 5 is an enlarged sectional view of an attachment part of the bellows packing member.

FIG. 4 shows a first example of the bellows packing member according to the present invention and FIG. 5 shows the bellows packing member attached to the artificial leg 10. The bellows packing member 70 of the first example will now be described with reference to those FIGS. 4 and 5.

The bellows packing member 70 is a molded product of chloroprene rubber. The bellows packing member 70 comprises an inner bead 72 for defining a hole large enough for passing the rod member 54 therethrough, an outer bead 74 concentrically surrounding the outside of the inner bead 72, and a bellows packing body part 76 disposed between the outer and inner beads 74, 72 and integrally connecting the outer and inner beads 74, 72. Each of the outer and inner beads 74, 72 serves as an attachment part and has a circular ring-like configuration in section. In contrast, the bellows packing body part 76 has a smaller thickness (for example, about 0.5 mm) than the radius of each bead and includes a plurality of irregular or wavy corrugations 78 for deformation. The corrugations 78 are arranged line symmetrically with respect to the inner bead 72. The height of each corrugation 78 is smaller (for example, about 2.5 mm) than the distance from the inner bead 72 to the outer bead 74, when the bellows packing body part 76 is in a non-deformed state.

The bellows packing member 70 are supported by being fit at the portion of the outer and inner beads 74, 72 thereof into the ring grooves thereby while retaining the sealing performance at the attachment parts. The outer bead 74 is fit into a ring groove 32 of the inner periphery of the shell structure 30, while the inner bead 72 is fit into a ring groove 82 of the outer periphery of a cylindrical rod guide 80. Here, the outer bead 74 is retained in a predetermined position even if the knee coupling 20 should bend. In contrast, the inner bead 72 moves in the predetermined radial directions (the directions as indicated by arrows X1 and X2 of FIG. 4) of the outer bead 74. Since the inner bead 72 makes such movement, there is a possibility that the inner bead 72 escapes from the ring groove 82. In order to prevent this possible occurrence, the ring groove 82 is preferably provided at an opening part thereof with an escape prevention stopper 84. The cylindrical rod guide 80 is supported on an upper part of the cylinder body 52 such that the expanding/contracting rod member 54 is guided by the guide surface 86 of the inner periphery.

The directions as indicated by arrows X1, X2 of FIG. 4 (i.e., the deforming directions of the bellows packing body part 76) correspond to the swinging directions of the rod member 54. In other words, the swinging directions are the predetermined directions and thus, when the knee coupling 20 moves, the bellows packing body part 76 receives a force directing in the predetermined directions in accordance with the swinging movement thereof.

Figure 6:
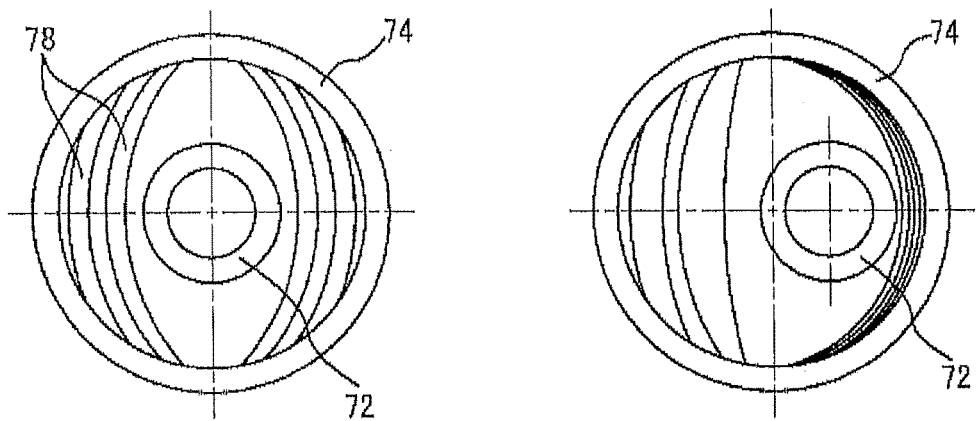
FIG. 6 is a plan view showing a second example of the bellows packing member.
Figure 7:
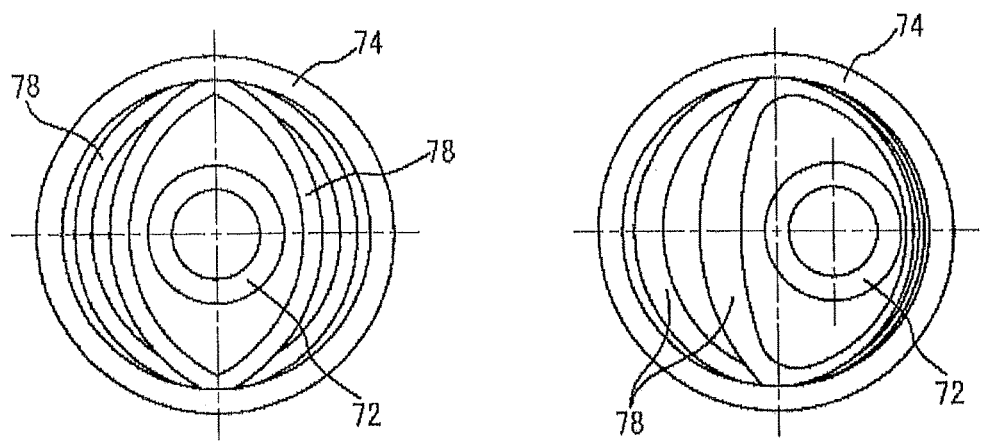
FIG. 7 is a plan view showing a third example of the bellows packing member.
Figure 8:
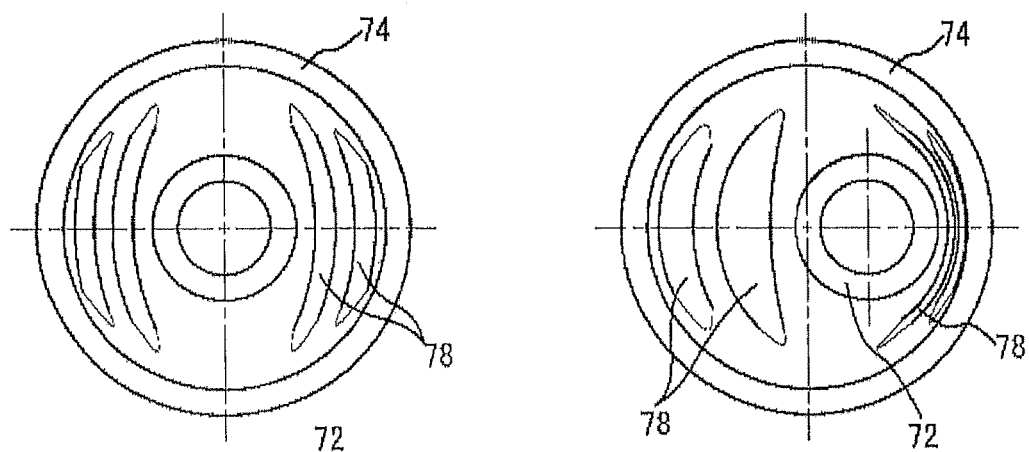
FIG. 8 is a plan view showing a fourth example of the bellows packing member.

In order to prevent noise from occurring caused by the deformation of the bellows packing member 70 to which the above-mentioned force is exerted, it is designed such that the deforming portion of the corrugations 78 will not adversely affect the rest portion continuous thereto or other corrugations. That is, each corrugation 78 is less curved than an imaginary circle between the inner and outer beads 74, 72 and both ends of each corrugation 78 extends or reaches the outer bead 74 or are located at positions closer to the outer bead 74 than the inner bead 72. In addition to the first example shown in FIG. 4, in the second example shown in FIG. 6 and in the third example shown in FIG. 7, the corrugations 78 are differently arranged and both ends of each corrugation 78 are connected to the outer bead 74. Moreover, in the example of FIG. 8, both ends of each corrugation 78 do not extend to or reach the outer bead 74.

Figure 9:
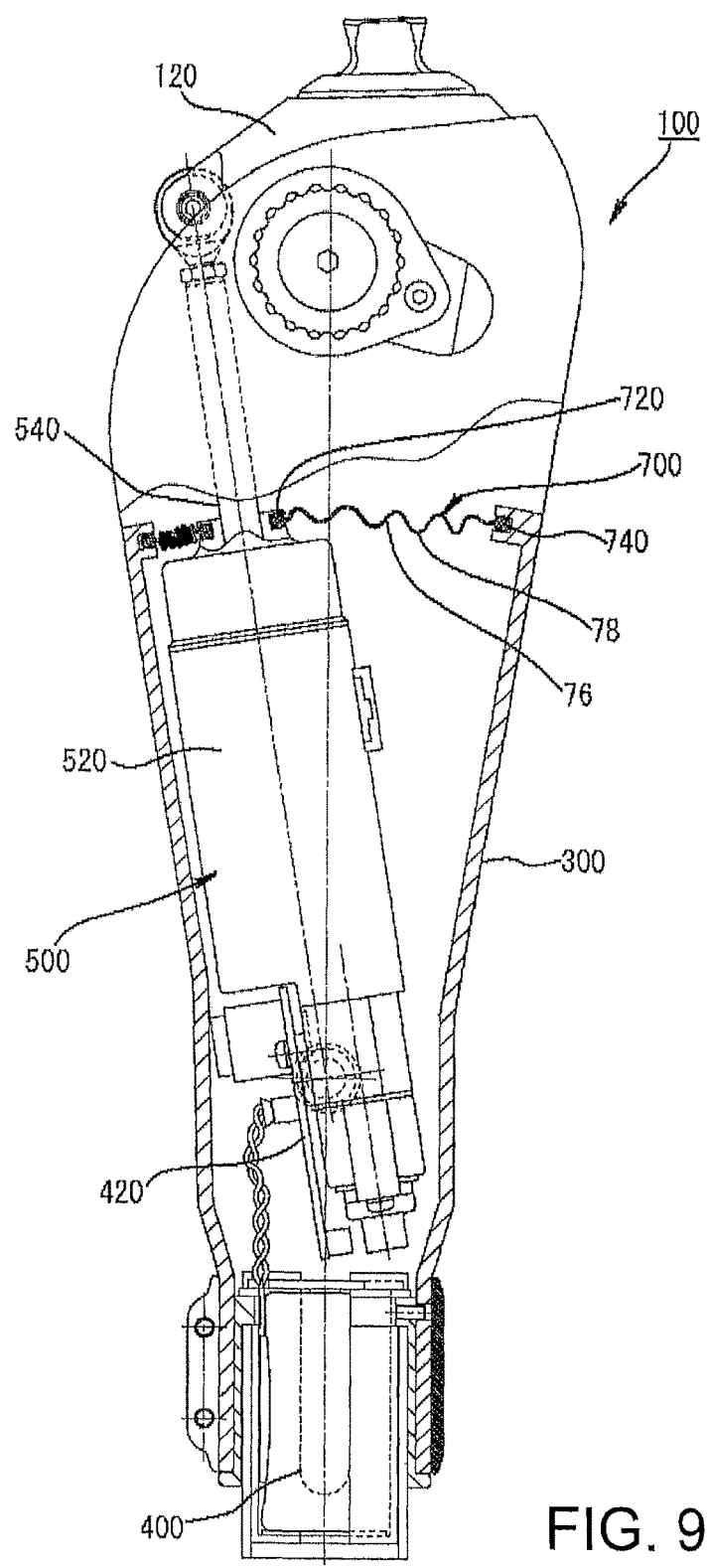
FIG. 9 is a sectional structural view of a single-axis connection artificial leg to which the present invention is applied.

Although description has been made with respect to the cases wherein the present invention is applied to a multi-axis artificial leg, the present invention can also be applied to a single-axis artificial leg. FIG. 9 shows one example of a single-axis artificial leg 100 according to the present invention. In this single-axis artificial leg 100, a battery 400, a control board 420, etc. for electronic control are built in an internal space of the shell structure 300 in addition to a cylinder body 520 of a pneumatic cylinder 500 (i.e., cylinder device).

A rod member 540 of the pneumatic cylinder 500 extends from the cylinder body 520 up to an upper member 120. Here again, in order to hermetically seal the upper opening part of the shell structure 300, a bellows packing member 700 is used. Since the bellows packing member 700 is larger in the amount of deformation required than the bellows packing member 70, the number of the corrugations 780 is doubled. However, the bellows packing member 700 is the same as the previously mentioned one in the respect that it comprises an inner bead 720, an outer bead 740 and a bellows packing body part 760 which connects the inner and outer beads 720, 740, that how those inner and outer beads 720, 740 are attached.

The power sources for the artificial legs 10, 100 are the batteries 40, 400 that are built in the shell structures 30, 300, respectively. These batteries are rechargeable and each provided with a recharging connector so that electric power can be fed from the outside of the shell structures 30, 300. Moreover, in order to provide a reliable sealing performance while simplifying the structure of the shell structures 30, 300, those batteries are unable to be exchanged by the user. Under such circumstance as just mentioned, in order to control the artificial leg stably, the remaining quantity of each battery should be kept more than a predetermined value. Power consumption of the battery can be divided into a motor system for varying the opening degree of a throttle valve of the cylinder device and a control microcomputer for controlling the motor system. The power consumption of the microcomputer is small, while that of the motor system is large.

The most important thing for the artificial leg is to operate as longer time as possible in a normal state. To this end, in addition to the built-in batteries, an external auxiliary power source (for example, portable batteries or the like) can be utilized. In that case, power can be equally fed to both the microcomputer and the motor system from the built-in batteries, which are the main power source, and the auxiliary power source. However, when the auxiliary power source is used (i.e., when the auxiliary power source is connected through the connector), it is preferable that the motor system which requires larger power consumption, uses only power of the auxiliary power source. Because, in doing so, by suppressing the consumption of the built-in battery as a main power source, a remaining quantity of more than a predetermined value can be obtained in the batteries themselves. Moreover, the possibility of the malfunction of the microcomputer caused by temporary voltage decrease which is caused by the operation of the motor system, even when the remaining quantity of the batteries is reduced. In addition, for the hermetically sealed type artificial leg, it is preferable from the view point of hermetical sealing that the connector for connecting the auxiliary power supply and the charging connector are formed into one connector and disposed at the inner side of the hermetically sealed cover 150 (FIG. 3) that can be opened/closed by the artificial leg wearer with respect to the shell structure.

DESCRIPTION OF REFERENCE NUMERALS

10 . . . multi-axis artificial leg
12 . . . upper member
14 . . . lower member
20 . . . knee coupling
30 . . . shell structure
50 . . . hydraulic cylinder (cylinder device)
52 . . . cylinder body
54 . . . rod member
70 . . . bellows packing member
72 . . . inner bead
74 . . . outer bead
76 . . . bellows packing body part
78 . . . corrugation
80 . . . rod guide
100 . . . single-axis artificial leg
120 . . . upper member
300 . . . shell structure
500 . . . pneumatic cylinder
520 . . . cylinder body
540 . . . rod member
700 . . . bellows packing member
720 . . . inner bead
740 . . . outer bead
760 . . . bellows packing body part
780 . . . corrugation

The invention claimed is:

1. A hermetically sealed artificial leg comprising:
an upper member for supporting a socket at an upper end thereof;
a lower member for supporting a foot part at a lower end thereof;
a knee coupling for bendably coupling said upper and lower members;
a cylinder device for assisting and/or limiting movement of said knee coupling;
a shell structure for surrounding an outside of said cylinder device;
said cylinder device including a cylinder body having an axis, and a rod member extending in a direction of said axis from said cylinder body, said rod member extending from inside of said shell structure to outside thereof; and
a flexible packing member for hermetically sealing a periphery of said rod member, wherein said flexible packing member includes:
an inner bead defining a hole for receiving said rod member therein and serving as a sealing portion at an inner periphery of said flexible packing member for hermetically sealing the periphery of said rod member;
an outer bead concentrically surrounding the outside of the inner bead, the outer bead serving as an attachment part to a side of said shell structure and also serving as a sealing portion for the side of said shell structure; and
a body portion formed between said inner and outer beads and integrally connecting said inner and outer beads, the body portion comprising a plurality of corrugations aligned with each other, and being configured for varying a distance between said inner and outer beads, and
wherein each of the plurality of corrugations is arc-shaped;
wherein each of the plurality of corrugations is positioned between the inner bead and the outer bead,
wherein both ends of each of the plurality of corrugations extend to the outer bead or are located at positions closer to the outer bead than the inner bead, and
wherein the plurality of corrugations are arranged line symmetrically with respect to a first line radially passing through the central axis of the inner bead, and the plurality of corrugations are arranged line symmetrically respect to a second line being perpendicular to the first line and radially passing through the central axis of the inner bead.

2. The hermetically sealed artificial leg of claim 1, wherein said shell structure and bellows packing member define a hermetically sealed space within said shell structure.

3. The hermetically sealed artificial leg of claim 2, wherein said artificial leg is configured to be electronically controlled, and, a part of an electronic control of the artificial leg is received in said hermetically sealed space.

4. The hermetically sealed artificial leg of claim 1, wherein when said upper and lower members move with respect to each other, said rod member is expanded and contracted in an axial direction of said cylinder body and at the same time, swung in a direction crossing said axis to deform said bellows packing body part.

5. The hermetically sealed artificial leg of claim 4, wherein, when said upper and lower members move with respect to each other, said inner bead is configured to move in a predetermined radial direction of said outer bead.

6. The hermetically sealed artificial leg of claim 1, wherein said cylinder body includes a rod guide for guiding said rod member, and said rod guide supports said inner bead.

7. The hermetically sealed artificial leg of claim 6, wherein said rod guide has a cylindrical shape and is provided, at an inner periphery of said rod guide, with a guide surface for guiding an outer periphery of said rod member and, at an outer periphery of said rod guide, with a ring groove into which said inner bead is received.

8. The hermetically sealed artificial leg of claim 7, wherein said ring groove is provided, at an opening part thereof, with a stopper adapted to retain said inner bead in the ring groove and to retain said inner bead in the ring groove during a movement of the inner bead caused by a movement of the knee coupling.

9. The hermetically sealed artificial leg of claim 1, wherein a rod end of said rod member of said cylinder device is located on a side of said upper member, while a cylinder head of said cylinder body of said cylinder device is located on a side of said lower member.

10. The hermetically sealed artificial leg of claim 9, wherein the inner bead has substantially the same height as the outer bead, in a sectional view taken along a longitudinal direction of the rod member.

11. The hermetically sealed artificial leg of claim 9, wherein the inner bead and the outer bead have different heights from each other, in a sectional view taken along a longitudinal direction of the rod member.

12. The hermetically sealed artificial leg of claim 1, wherein each of the plurality of corrugations in said bellows packing body part maintains the same height from said inner bead to said outer bead.

13. The hermetically sealed artificial leg of claim 12, wherein a height of each of the plurality of corrugations is smaller than a distance from said inner bead to said outer bead, when said bellows packing body part is in a non-deformed state.

14. The hermetically sealed artificial leg of claim 1, wherein connection of said knee coupling includes a single-axis connection or a multi-axis connection.

15. The hermetically sealed artificial leg of claim 1, wherein said cylinder device is selected from the group consisting of a hydraulic cylinder, a spring cylinder, a pneumatic cylinder and a linear actuator.

\* \* \* \* \*